(12) United States Patent
DiLuccio

(10) Patent No.: US 12,302,902 B2
(45) Date of Patent: May 20, 2025

(54) ANTIMICROBIAL COMPOSITIONS, INCLUDING ANTIMICROBIAL HYDROGELS, EFFECTIVE AGAINST MATURE BIOFILMS

(71) Applicant: Cormedix Inc., Berkeley Heights, NJ (US)

(72) Inventor: Robert DiLuccio, Haymarket, VA (US)

(73) Assignee: CorMedix Inc., Berkeley Heights, NJ (US)

( * ) Notice: Subject to any disclaimer, the term of this patent is extended or adjusted under 35 U.S.C. 154(b) by 0 days.

(21) Appl. No.: 15/861,159

(22) Filed: Jan. 3, 2018

(65) Prior Publication Data
US 2018/0184656 A1 Jul. 5, 2018

Related U.S. Application Data

(60) Provisional application No. 62/442,775, filed on Jan. 5, 2017.

(51) Int. Cl.
| | | |
|---|---|---|
| *A01N 43/88* | (2006.01) | |
| *A01N 37/02* | (2006.01) | |
| *C07D 285/18* | (2006.01) | |
| *C08B 37/08* | (2006.01) | |
| *C08J 3/075* | (2006.01) | |
| *C09D 5/14* | (2006.01) | |
| *C09D 5/16* | (2006.01) | |
| *C09D 105/08* | (2006.01) | |

(52) U.S. Cl.
CPC ............ *A01N 43/88* (2013.01); *A01N 37/02* (2013.01); *C07D 285/18* (2013.01); *C08B 37/0072* (2013.01); *C08J 3/075* (2013.01); *C09D 5/14* (2013.01); *C09D 5/16* (2013.01); *C09D 105/08* (2013.01); *A61L 2400/18* (2013.01)

(58) Field of Classification Search
CPC .................................................... A01N 43/88
See application file for complete search history.

(56) References Cited

U.S. PATENT DOCUMENTS

| | | | |
|---|---|---|---|
| 6,475,434 B1 | 11/2002 | Darouiche | |
| 7,314,857 B2 | 1/2008 | Madhyastha | |
| 8,529,935 B2 * | 9/2013 | Giammona | A61L 27/54 |
| | | | 514/354 |
| 2004/0156908 A1 | 8/2004 | Polaschegg | |
| 2005/0049181 A1 | 3/2005 | Madhyastha | |
| 2011/0311647 A1 | 12/2011 | Gawande et al. | |
| 2013/0084319 A1 | 4/2013 | Priewe et al. | |
| 2013/0085469 A1 | 4/2013 | Polaschegg | |
| 2013/0129800 A1 | 5/2013 | Giammona et al. | |
| 2013/0302390 A1 | 11/2013 | Davies | |
| 2015/0182667 A1 | 7/2015 | Guelcher et al. | |
| 2017/0100407 A1 * | 4/2017 | Reidenberg | A61K 47/12 |
| 2019/0046488 A1 * | 2/2019 | Rosenblatt | A61K 45/06 |

FOREIGN PATENT DOCUMENTS

| | | |
|---|---|---|
| EP | 1 442 753 | 8/2004 |
| KR | 2015-0110843 A * | 10/2015 |
| WO | WO 00/33895 | 6/2000 |
| WO | WO 2005/115357 | 12/2005 |
| WO | WO 2008/043175 | 4/2008 |
| WO | WO 2008/143889 | 11/2008 |
| WO | WO 2012/014180 | 2/2012 |
| WO | WO 2013/009998 | 1/2013 |
| WO | WO 2013/049149 | 4/2013 |
| WO | WO 2015/168677 | 11/2015 |

OTHER PUBLICATIONS

Anwar, H. et al., Dynamic interactions of biofilms of mucoid Pseudomonas aeruginosa with tobramycin and piperacillin, Antimicrob. Agents Chemother., vol. 36, 1992, pp. 1208-1214.

Carrel, M. et al., Biofilm imaging in porous media by laboratory X-Ray tomography: Combining a non-destructive contrast agent with propagation-based phass-contrast imaging tool, PLoS ONE, vol. 12, No. 7, e0180374, 2017, pp. 1-18.

Cirioni et al., Daptomycin and Rifampin Alone and in Combination Prevent Vascular Graft Biofilm Formation and Emergence of Antibiotic Resistance in a Subcutaneous Rate Pouch Model of Staphylococoocal Infection, European Journal of Vascular and Endovascular Surgery. vol. 6. Iss. 6, 2010, pp. 817-822.

Darouiche, R.O. et al., A comparison of two antimicrobial-impregnanted central venous catheters, N. Engl. J. Med., vol. 340, No. 1, 1999, pp. 1-8.

Hausner, M. et al., High Rates of Conjugation in Bacterial Biofilms as Determined by Quantitative In Situ Analysis, Applied and Environmental Microbiolgy, vol. 65, No. 8, 1999, pp. 3710-3713.

Maki, D.G., In Vitro Studies of a Novel Antimicrobial Luer-Activated Needleless Connector for Prevention of Catheter-Related Bloodstream Infection, Clinical Infection Diseases, vol. 50, Iss. 12, 2010, pp. 1580-1587.

Roberts. A.P. et al., Characterization of the Ends of Target Site of a Novel Tetracycline Resistance-Encoding Conjugative Transposon from Enterococcus faecium 644.1H1, J. of Bacteriology, vol. 168, No. 12. 2006, pp. 4356-4361.

Stickler, D.J. et al., The Structure of Urinary Catheter Encrusting Bacterial Biofilms, Cells and Materials, vol. 3, Iss. 3, 1993, pp. 315-320.

(Continued)

*Primary Examiner* — Sarah Alawadi
(74) *Attorney, Agent, or Firm* — Pandiscio & Pandiscio

(57) ABSTRACT

A method for the prevention or elimination of biofilm microorganisms on at least one surface of a medical device, the method comprising the steps of: (a) providing a biofilm-active composition having at least one biofilm-active agent; and (b) delivering the biofilm-active composition to the medical device in an amount sufficient to prevent or eliminate the biofilm microorganisms on at least one surface of the medical device.

5 Claims, 4 Drawing Sheets

(56) References Cited

OTHER PUBLICATIONS

Brisset, L. et al., In vivo and in vitro analysis of the ability of urinary catheter to microbial colonization, Pathol Biol (Paris), vol. 44, No. 5, 1996, pp. 397-404.

Costerton, J.W. et al., Bacterial Biofilms: A Common Cause of Persistent Infections, Science, vol. 284, 1999, pp. 1318-1322.

Elliot, T.S.J., Novel approach to investigate a source of microbial contamination of central venous catheters, Eur. J. Clin. Microbiol. Infect. Dis., vol. 16, No. 3, 1997. pp. 210-213.

Flowers, R.H. et al., Efficacy of an attachable subcutaneous cuff for the prevention of intravascular catheter-related infection, JAMA, vol. 261, No. 6. 1989, pp. 878-883.

Kamal, G.D. et al., Reduced intravascular catheter infection by antibiotic bonding, A prospective, randomized, controlled trial, JAMA, vol. 265, 1991, pp. 2364-2368.

Morris, N.S. et al., Encrustation of indwelling urethral catheters by Proteus mirabilis biofilms growing in human urine, J. Hosp. Infect., vol. 39, Iss. 3, 1998, pp. 227-234.

Raad, I., Intravascular-catheter-related infections, Lancet., vol. 351, No. 9106, 1998, pp. 893-898.

Raad, I. et al., Quantitative tip culture methods and the diagnosis of central venous catheter-related infections, Diagn. Microbial. Infect. Dis., vol. 15, Iss. 1, 1992, pp. 13-20.

Tunney, M.M. et al., Biofilm and biofilm-related encrustation of urinary tract devices, Methods Enzymol., vol. 310, 1999, pp. 558-566.

Drago et al., "Antiadhesive and antibiofilm activity of hyaluronic acid against bacteria responsible for respiratory tract infections", APMIS, vol. 122, No. 10, 2014, pp. 1013-1019.

Perez-Giraldo et al. "Influence of N-acetylcysteine on the formation of biofilm by *Staphylococcus epidermidis*", J. Antimicrobial Chemotherapy, vol. 39, 1997, pp. 643-646.

Koo et al., "Targeting microbial biofilms: current and prospective therapeutic strategies", Nat Rev Microbiol, vol. 15, No. 12, 2017, pp. 740-755.

Rodriguez-Beltran et al., "N-Acetylcysteine Selectively Antagonizes the Activity of Imipenem in Pseudomonas aeruginosa by an OprD-Mediated Mechanism", Antimicrobial Agents and Chemotherapy, vol. 59, No. 6, 2015, pp. 3246-3251.

Liaw S. et al., Modulation of Swarming and Virulence by Fatty Acids through the RsbA Protein in Proteus mirabilis, Infection and Immunity, Dec. 2004, vol. 72, No. 12, pp. 6836-6845.

Inoue T. et al., Inhibition of swarming motility of Pseudomonas aeruginosa by branched-chain fatty acids, FEMS Microbiology Letters, Mar. 2008, vol. 281, No. 1, pp. 81-86.

Cassandro E. et al., Hyaluronan in the Treatment of Chronic Rhinosinusitis with Nasal Polyposis, Indian Journal of Otolaryngology and Head & Neck Surgery, Sep. 2015, vol. 67, No. 3, pp. 299-307.

* cited by examiner

Activity of taurolidine loaded hydrogels against biofilm on a Pig Skin Explant Model

| | | | | | |
|---|---|---|---|---|---|
| 1 LMW HA Cntr | 4 0.5% Taurolidine | 7 1.0% Taurolidine | 10 1.5% Taurolidine | 13 1% Taurolidine 0.25% MRA | |
| 2 MMW HA Cntr | 5 0.5% Taurolidine | 8 1.0% Taurolidine | 11 1.5% Taurolidine | 14 1% Taurolidine 0.25% MRA | |
| 3 HMW HA Cntr | 6 0.5% Taurolidine | 9 1.0% Taurolidine | 12 1.5% Taurolidine | 15 1% Taurolidine 0.25% MRA | |

FIG. 3

ANTIMICROBIAL COMPOSITIONS, INCLUDING ANTIMICROBIAL HYDROGELS, EFFECTIVE AGAINST MATURE BIOFILMS

REFERENCE TO PENDING PRIOR PATENT APPLICATION

This patent application claims benefit of U.S. Provisional Patent Application Ser. No. 62/442,775, filed Jan. 5, 2017 by Cormedix, Inc. and Robert DiLuccio for ANTIMICROBIAL COMPOSITIONS, INCLUDING ANTIMICROBIAL HYDROGELS, EFFECTIVE AGAINST MATURE BIOFILMS, which patent application is hereby incorporated herein by reference.

FIELD OF THE INVENTION

This invention relates to microbial biofilms in general, and more particularly to compositions for use in inhibiting microbial biofilms.

BACKGROUND OF THE INVENTION

Microbial biofilms develop when microorganisms irreversibly adhere to a submerged surface and produce extracellular polymers that facilitate adhesion and provide a structural matrix. This submerged surface may be inert, non-living material or living tissue. Biofilm-associated microorganisms behave differently from planktonic (i.e., freely suspended) organisms with respect to growth rates and the ability to resist antimicrobial treatments, and therefore pose a public health problem. Microbial biofilms can develop on or within indwelling medical devices (e.g., contact lenses, central venous catheters and needleless connectors, endotracheal tubes, intrauterine devices, mechanical heart valves, pacemakers, peritoneal dialysis catheters, prosthetic joints, tympanostomy tubes, urinary catheters, guides used in neurological procedures, etc.).

Biofilms on indwelling medical devices may comprise gram-positive or gram-negative bacteria or yeasts. Bacteria commonly isolated from these indwelling medical devices include the gram-positive bacteria *Enterococcus faecalis, Staphylococcus aureus, Staphylococcus epidermidis,* and *Streptococcus viridans,* and the gram-negative bacteria *Escherichia coli, Klebsiella pneumoniae, Proteus mirabilis,* and *Pseudomonas aeruginosa*. These organisms may originate from the skin of patients or healthcare workers, tap water to which entry ports are exposed, or other sources in the environment. Biofilms may comprise a single species of microorganism or multiple species of microorganisms, depending on the indwelling medical device and its duration of use in the patient. Urinary catheter biofilms may initially comprise a single species of microorganism, but longer exposures inevitably lead to multispecies biofilms.

A distinguishing characteristic of biofilms is the presence of extracellular polymeric substances, primarily polysaccharides, surrounding and encasing the cells of the microorganisms. Most biofilm volume is actually composed of this extracellular polymeric substance rather than the cells of the microorganisms. This biofilm matrix may act as a filter, entrapping minerals or host-produced serum components. Biofilms are both tenacious and highly resistant to antimicrobial treatment. Anwar et al. showed that treatment with levels of tobramycin far in excess of the minimum inhibitory concentration (MIC) reduced biofilm cell counts for *P. aeruginosa* by approximately 2 "logs", while the same dosage provided a >8 "log" decrease in planktonic cells of this organism (Anwar H, Strap J L, Chen K, Costerton J W. Dynamic interactions of biofilms of mucoid *Pseudomonas aeruginosa* with tobramycin and piperacillin, Antimicrob Agents Chemother, 1992; 36:1208-14).

When an indwelling medical device is contaminated with microorganisms, several variables determine whether a biofilm develops. First, the microorganisms must adhere to the exposed surfaces of the device long enough to become irreversibly attached. The rate of cell attachment depends on the number and types of cells in the liquid to which the device is exposed, the flow rate of the liquid through the device, and the physicochemical characteristics of the exposed surface of the device. Components in the liquid may alter the surface properties and also affect the rate of cell attachment. Once these cells irreversibly attach to the indwelling device and produce extracellular polysaccharides to develop a biofilm, the rate of growth of the biofilm is influenced by flow rate, the nutrient composition of the medium, antimicrobial-drug concentration, and the ambient temperature. These factors can be illustrated by examining what is known about biofilms on three types of indwelling medical devices: central venous catheters, mechanical heart valves, and urinary (i.e., Foley) catheters.

Central Venous Catheters

Scanning and transmission electron microscopy has shown that virtually all indwelling central venous catheters are colonized by microorganisms embedded in a biofilm matrix. The organisms most commonly isolated from catheter biofilms are *Staphylococcus epidermidis, S. aureus, Candida albicans, P. aeruginosa, K. pneumoniae,* and *Enterococcus faecalis.*

These organisms originate from a patient's skin microflora, exogenous microflora from healthcare personnel, or contaminated infusates. They gain access to the catheter by migration, externally from the skin along the exterior catheter surface, or internally from the catheter hub or port. Colonization of these devices can occur rapidly, and may be a function of host-produced conditioning films (e.g., platelets, plasma, tissue proteins, etc.). Raad et al. found that biofilm formation on central venous catheters was universal, but the extent and location of biofilm formation depended on the duration of catheterization: short-term (<10 days) catheters had greater biofilm formation on the external surface of the catheters, long-term catheters (>10 days, e.g., 30 days) had more biofilm formation on the inner lumen of the catheters. The nature of the fluid administered through central venous catheters may affect microbial growth: gram-positive organisms (e.g., *S. epidermidis,* and *S. aureus*) did not grow well in intravenous fluids, whereas gram-negative aquatic organisms (e.g., *P. aeruginosa, Klebsiella* spp., *Enterobacter* spp., *Serratia* spp., and *Pantoea* sp.) sustained growth (Raad I. Intravascular-catheter-related infections, Lancet. 1998; 351(9106)893-8; Raad I I, Sabbagh M F, Rand K H, Sherertz R J. Quantitative tip culture methods and the diagnosis of central venous catheter-related infections. Diagnostic Microbiol Infect Dis. 1992; 15(1)13-20).

Several studies have examined the effect of various types of antimicrobial treatments in controlling biofilm formation on these devices. Freeman and Gould found that the addition of sodium metabisulfite to the dextrose-heparin flush of a left atrial catheter eliminated microbial colonization of the catheter (Freeman R, Gould F K. Infection and intravascular catheters [letter]. J Antimicrob Chemother. 1985; 15:258). Darouiche et al. found that catheters impregnated with minocycline and rifampin were less likely to be colonized than those impregnated with chlorhexidine and silver sulfadiazine (Darouiche R O, Raad I I, Heard S O, Thornby J I, Wenker O C, Gabrielli A, A comparison of two antimicrobial-impregnated central venous catheters. N Engl J Med. 1999; 340:1-8). Kamal et al. found catheters coated with a cationic surfactant (tridodecylmethylammonium chloride) were less likely to become contaminated and develop biofilms than were untreated catheters (Kamal G D, Pfaller M A, Rempe L E, Jebson P J R. Reduced intravascular catheter infection by antibiotic bonding. A prospective, randomized, controlled trial. JAMA. 1991; 265:2364-8). Flowers et al. found that an attachable subcutaneous cuff containing silver ions inserted after local application of polyantibiotic ointment conferred a protective effect on catheters, resulting in lower rates of contamination (Flowers R H, Schwenzer K J, Kopel R F, Fisch M J, Tucker S I, Farr B M. Efficacy of an attachable subcutaneous cuff for the prevention of intravascular catheter-related infection. JAMA. 1989; 261:878-83). Maki suggested several ways to control biofilms on central venous catheters, including using aseptic techniques during implantation, using topical antibiotics, minimizing the duration of catheterization, using an in-line filter for intravenous fluids, creating a mechanical barrier to prevent the influx of organisms by attaching the catheter to a surgically-implanted cuff, coating the inner lumen of the catheter with an antimicrobial agent, and removing the contaminated device (Maki, Dennis G. In Vitro Studies of a Novel Antimicrobial Luer-Activated Needless Connector for Prevention of Catheter-Related Bloodstream Infection. Clinical Infectious Diseases 50(12) 1580-1587).

Mechanical Heart Valves

Microorganisms may attach to, and develop biofilms on, components of mechanical heart valves and surrounding tissues of the heart, leading to a condition known as prosthetic valve endocarditis. The primary organisms responsible for this condition are *S. epidermidis, S. aureus, Streptococcus* spp., gram-negative bacilli, diphtheroids, enterococci, and *Candida* spp. These organisms may originate from the skin, other indwelling devices such as central venous catheters, or dental work. The identity of the causative microorganism is related to its source: whether the contaminating organism originated at the time of surgery (early endocarditis, usually caused by *S. epidermidis*), from an invasive procedure such as dental work (*Streptococcus* spp.), or from an indwelling device (a variety of organisms). Implantation of the mechanical heart valve causes tissue damage, and circulating platelets and fibrin tend to accumulate where the valve has been attached. Microorganisms also have a greater tendency to colonize these locations. The resulting biofilms more commonly develop on the tissue surrounding the prosthesis, or on the sewing cuff fabric used to attach the device to the tissue, rather than on the valve itself. Antimicrobial agents are usually administered during valve replacement, and whenever the patient has dental work, in order to prevent initial attachment of the microorganisms at the surgical site by killing all of the microorganisms introduced into the bloodstream. As with biofilms on other indwelling devices (e.g., central venous catheters), relatively few patients can be cured of a biofilm infection by antibiotic therapy alone. Illingworth et al. found that a silver-coated sewing cuff on a St. Jude mechanical heart valve (St. Jude Medical Inc., St. Paul, MN) implanted into a guinea pig artificially infected with *S. epidermidis* produced less inflammation than did uncoated fabric. Although the number of attached organisms was not determined, the authors concluded that the degree of inflammation was proportional to the number of viable organisms (Illingworth B L, Tweden K, Schroeder R F, Cameron J D. In vivo efficacy of silver-coated (Silzone) infection-resistant polyester fabric against a biofilm-producing bacteria, *Staphylococcus epidermidis*. J Heart Valve Dis. 1998; 7:524-30). Carrel et al. also found this approach was effective in in vitro studies with different organisms. (See PLoS ONE 12(7)p e0180374).

Urinary (Foley) Catheters

Urinary catheters are tubular latex or silicone devices which, when inserted into a patient, may readily acquire biofilms on the inner and/or outer surfaces thereof. The organisms commonly contaminating these devices and developing biofilms thereon are *S. epidermidis, Enterococcus faecalis, E. coli, Proteus mirabilis, P. aeruginosa, K. pneumoniae*, and other gram-negative organisms. The longer the urinary catheter remains in place, the greater the tendency of these organisms to develop biofilms and result in urinary tract infections in a patient. For example, 10% to 50% of patients undergoing short-term urinary catheterization (e.g., 7 days or less) become infected, and virtually all patients undergoing long-term catheterization (e.g., >28 days) become infected.

Brisset et al. found that adhesion to catheter materials was dependent on the hydrophobicity of both the organisms and the catheter surfaces. Catheters displaying both hydrophobic and hydrophilic regions allowed colonization of the widest variety of organisms. Divalent cations (e.g., calcium and magnesium), an increase in urinary pH, and ionic strength all resulted in an increase in bacterial attachment to catheter materials (Brisset L, Vernet-Garnier V, Carquin J, Burde A, Flament J B, Choisy C. In vivo and in vitro analysis of the ability of urinary catheters to microbial colonization. Pathol Biol (Paris). 1996; 44:397-404). Tunney et al. stated that, when looking at silicone, polyurethane, composite biomaterials, or hydrogel-coated materials, no one of those materials is more effective in preventing colonization than any other one of those materials. Certain component organisms of these biofilms produce urease, which hydrolyzes the urea in the patient's urine to ammonium hydroxide. The elevated pH that results at the biofilm-urine interface results in precipitation of minerals such as struvite and hydroxyapatite. These mineral-containing biofilms form encrustations that may completely block the inner lumen of the catheter. Bacteria may ascend the inner lumen into the patient's bladder in 1 to 3 days. This rate may be influenced by the presence of swarming organisms such as *Proteus* spp. (Tunney M M, Jones D S, Gorman S P. Biofilm and biofilm-related encrustation of urinary tract devices. In: Doyle R J, editor. Methods in enzymology. San Diego: Academic Press; 1999. p. 558-66).

Several strategies have been attempted to control urinary catheter biofilms: antimicrobial ointments and lubricants, bladder instillation or irrigation, antimicrobial agents in collection bags, impregnation of the catheter with antimicrobial agents such as silver oxide, or use of systemic antibiotics. Most such strategies have been ineffective, although silver-impregnated catheters delayed the onset of bacteriuria for up to 4 days. In a rabbit model, biofilms on Foley catheter surfaces were highly resistant to high levels of amdinocillin, a beta-lactam antibiotic. Stickler et al. found that treatment of a patient with a polymicrobial biofilm-infected catheter with ciprofloxacin allowed the catheter to clear and provide uninterrupted drainage for 10 weeks (Stickler D J, King J, Nettleton J, Winters C. The structure of urinary catheter encrusting bacterial biofilms. Cells and Materials. 1993; 3:315-9). Morris et al. found that the time-to-blockage of catheters in a laboratory model system was shortest for hydrogel- or silver-coated latex catheters and longest for an Eschmann Folatex S All Silicone catheter (Portex Ltd., Hythe, Kent, England). (Journal of Hospital Infection 39(3)227-234). Biofilms of several gram-negative organisms were reduced by exposure to mandelic acid plus lactic acid. In their studies, ciprofloxacin-containing liposomes were coated onto a hydrogel-containing Foley catheter and exposed in a rabbit model, the time to develop bacteriuria was double that of untreated catheters, although infection ultimately occurred in the rabbits with treated catheters.

Additional Comments about Biofilms

Bacteria within biofilms are intrinsically more resistant to antimicrobial agents than planktonic cells because of the diminished rates of mass transport of antimicrobial molecules to the biofilm associated cells (or because biofilm cells differ physiologically from planktonic cells). Antimicrobial concentrations sufficient to inactivate planktonic organisms are generally inadequate to inactivate biofilm organisms, especially those deep within the biofilm, potentially selecting for resistant subpopulations. This selection may have implications for treatments that use a controlled release of antimicrobial agents to prevent biofilm growth on indwelling devices. Bacteria can transfer extachromosomal genetic elements within biofilms. Roberts et al. demonstrated transfer of a conjugative transposon in a model oral biofilm. (Journal of Bacteriology 188(12)4356-4361). Hausner and Wuertz demonstrated conjugation in a lab-grown biofilm with rates one to three orders of magnitude higher than those obtained by classic plating techniques. Resistance-plasmids could also be transferred within biofilms on indwelling medical devices. (Applied and Environmental Microbiology 65(8)37120-3713).

SUMMARY OF INVENTION

The present invention comprises the provision and use of a novel composition for substantially preventing the growth or proliferation of biofilm-embedded microorganisms on a medical device, wherein the novel composition comprises at least one biofilm-active agent.

A further feature of the present invention is that the novel composition may be applied to a base material, wherein the base material may comprise a portion of the medical device, or wherein the base material may comprise a carrier material.

Another feature of the present invention is that the at least one biofilm-active agent of the novel composition may be selected from the group consisting of taurolidine and derivatives thereof.

A further feature of the present invention is that the base material may be selected from the group consisting of rubbers, thermoplastics, and elastomers.

Another feature of the present invention is that the base material may be selected from a variety of buffer solutions.

In accordance with the present invention, the novel composition may remove substantially all of the biofilm-embedded microorganisms from a medical device.

A further feature of the present invention is that the biofilm-active agent of the novel composition may be formed by mixing taurolidine or derivatives thereof and a base material.

An additional feature of the present invention is that the biofilm-active composition may be fashioned to a medical device for a period of time sufficient to form a coating of the biofilm-active composition on at least one surface of the medical device.

Another feature of the present invention is that the biofilm-active composition may be contacted to a medical device by integrating the biofilm-active composition with the material forming the medical device during formation of the medical device.

In accordance with the present invention, a system may be provided which comprises (a) a medical device; and (b) a biofilm-active composition coating for substantially preventing the growth or proliferation of biofilm-embedded microorganisms on at least one surface of the coated medical device, the biofilm-active composition coating being disposed upon the at least one surface of the medical device.

The biofilm-active composition, the method for coating medical devices, and the method for removing substantially all biofilm-embedded microorganisms from at least one surface of medical devices, when compared with previously-proposed biofilm-active compositions, and when compared with previously-proposed methods of removing substantially all biofilm-embedded microorganisms from at least one surface of medical devices, have the advantages of: (i) providing disruption of the biofilm, thereby allowing antimicrobial agents and/or antifungal agents to penetrate the biofilm and remove biofilm-embedded microorganisms from surfaces of medical devices; and (ii) preventing the growth or proliferation of biofilm-embedded microorganisms from surfaces of medical devices.

A further feature of the present invention is that the biofilm-active composition may further comprise a biofilm-penetrating agent for enhancing the ability of the biofilm-active composition to penetrate into and break up the biofilm. The biofilm-penetrating agent may comprise long-chain or short-chain fatty acids or fatty alcohols.

In one preferred form of the present invention, the biofilm-active composition comprises a biofilm-active agent in the form of taurolidine and derivatives thereof, and a biofilm-penetrating agent in the form of long-chain or short-chain fatty acids or fatty alcohols.

Thus, the present invention comprises (i) the provision of biofilm-active compositions for preventing the growth or proliferation of biofilm-embedded microorganisms on a medical device, and (ii) the use of biofilm-active compositions on a medical device for preventing the growth or proliferation of biofilm-embedded microorganisms on a medical device. In one preferred form of the invention, the biofilm-active composition comprises taurolidine or derivatives thereof. And in one preferred form of the invention, the biofilm-active composition comprises a biofilm-penetrating agent for facilitating penetration into, and breaking up of, the biofilm. In one preferred form of the invention, the biofilm penetrating agent comprises long-chain or short-chain fatty acids or fatty alcohols.

In one preferred form of the invention, there is provided a method for the prevention or elimination of biofilm microorganisms on at least one surface of a medical device, the method comprising the steps of:

(a) providing a biofilm-active composition having at least one biofilm-active agent; and (b) delivering the biofilm-active composition to the medical device in an amount sufficient to prevent or eliminate the biofilm microorganisms on at least one surface of the medical device.

In another preferred form of the invention, there is provided a biofilm-active and biofilm-penetrating composition having at least one biofilm-active agent and at least one biofilm-penetrating agent, wherein the biofilm-active and biofilm-penetrating composition is formed by mixing taurolidine or its derivatives thereof, a biofilm-penetrating agent, and a base material.

In another preferred form of the invention, there is provided a system comprising:
a medical device; and
a biofilm-active and biofilm-penetrating composition applied to the medical device, wherein the biofilm-active and biofilm-penetrating composition comprises at least one biofilm-active agent.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 3 is a table showing the efficacy of various taurolidine formulations, wherein the taurolidine formulations comprise taurolidine and myristic acid in a hyaluronic acid gel.

DETAILED DESCRIPTION OF THE PREFERRED EMBODIMENTS

Figure 1:
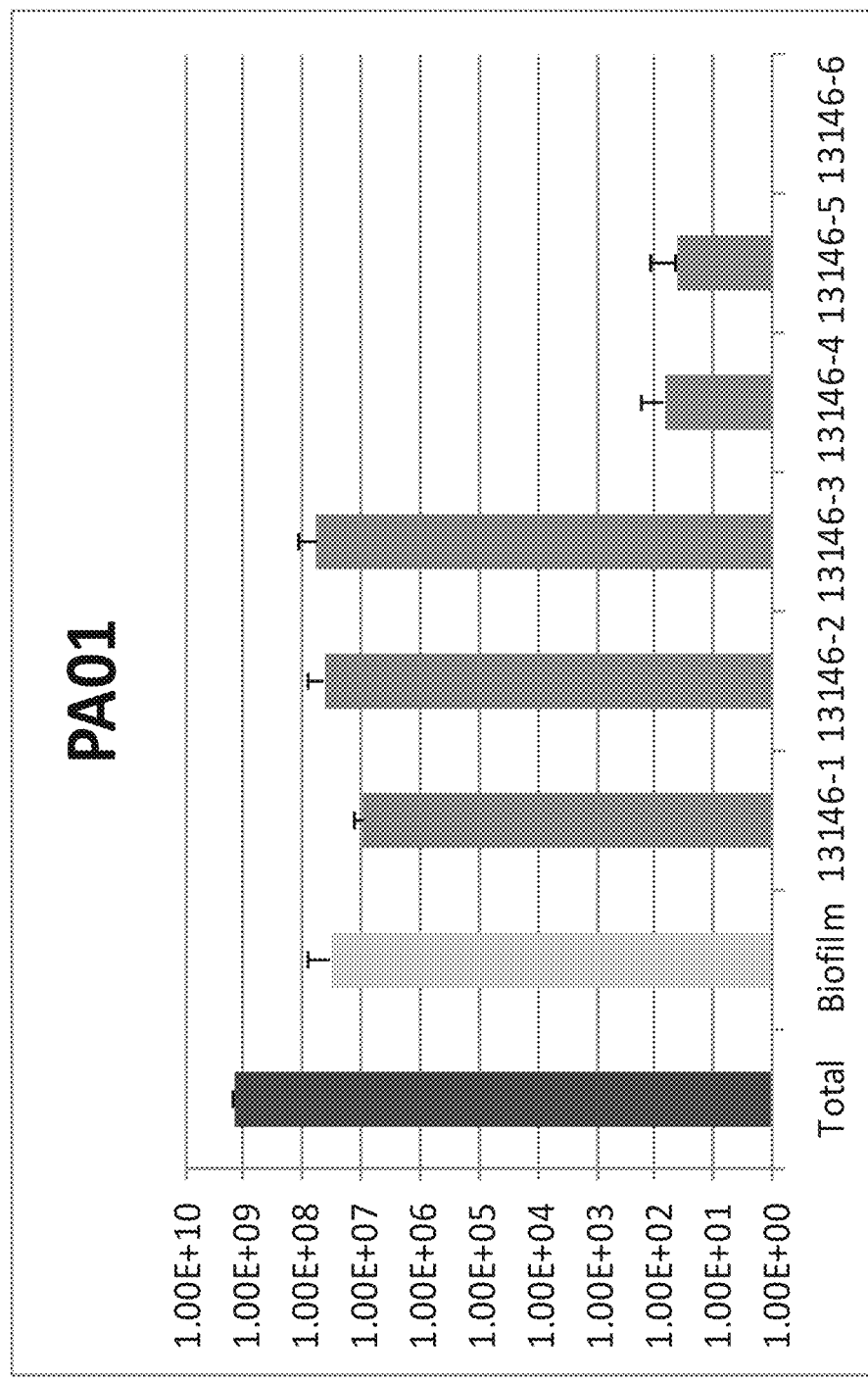
FIG. 1 is a graph showing the activity of taurolidine-loaded hydrogels against biofilm on a Pig Skin Explant Model.

In one preferred form of the invention, the present invention is directed to a biofilm-active and a biofilm-penetrating composition which may be in the form of (i) a coating which is applied to medical devices and which substantially prevents biofilm-embedded microorganisms from growing and proliferating on at least one surface of the medical devices, and/or (ii) in the form of a flowable composition which is flowed to the site of the medical device and which substantially facilitates access of antimicrobial agents to the biofilm-embedded microorganisms in order to assist in the prevention of the biofilm-embedded microorganisms from growing or proliferating on at least one surface of a medical device.

The biofilm-active and biofilm-penetrating composition may also be in the form of a liquid, or solution, which is used to clean medical devices, which includes biofilm-embedded microorganisms living and proliferating on at least one surface of the medical devices, by flushing, rinsing, soaking, and/or any other cleaning methods known to persons skilled in the art, and thus remove the biofilm-embedded microorganisms from at least one surface of the medical device.

Broadly speaking, the biofilm-active and biofilm-penetrating composition includes (i) a biofilm-active agent (e.g., taurolidine) which is an antimicrobial, and (ii) a biofilm-penetrating agent (e.g., long-chain or short-chain fatty acids or fatty alcohols), which, in its activated state, disrupts the biofilm of microorganisms and attacks the microorganisms and/or allows other antimicrobial agents (e.g., antiseptics or antibiotics or antifungal agents present in the biofilm-active and biofilm-penetrating composition) to remove the biofilm-embedded microorganisms from at least one surface of the medical devices, and/or prevents the growth or proliferation of biofilm-embedded microorganisms on at least one surface of the medical devices. Specifically, the biofilm-active and biofilm-penetrating composition coating for medical devices may be formulated to substantially prevent the proliferation of biofilm-embedded microorganisms on, and/or to remove substantially all of the microorganisms from, the surfaces of medical devices.

The term "biofilm-embedded microorganisms" as used herein may include any microorganism which forms a biofilm during colonization and proliferation on the surface of medical devices including, but not limited to, gram-positive bacteria (such as *Staphylococcus epidermidis*), gram-negative bacteria (such as *Pseudomonas aeruginosa*), and/or fungi (such as *Candida albicans*). While the biofilm-active and biofilm-penetrating composition coating may include only biofilm-active and biofilm-penetrating agents, the biofilm-active and biofilm-penetrating composition coating preferably includes a base material, a biofilm-active agent and a biofilm-penetrating agent. Note that the base material may comprise part of the indwelling medical device, or the base material may comprise a carrier material (e.g., a hydrogel).

The term "medical devices" as used herein may include disposable or permanent catheters, (e.g., central venous catheters, dialysis catheters, long-term tunneled central venous catheters, short-term central venous catheters, peripherally-inserted central catheters, peripheral venous catheters, pulmonary artery Swan-Ganz catheters, urinary catheters, peritoneal catheters, etc.), long-term urinary devices, tissue-bonding urinary devices, vascular grafts, vascular catheter ports, wound drain tubes, ventricular catheters, hydrocephalus shunts, heart valves, heart-assist devices (e.g., left ventricular assist devices), pacemaker capsules, incontinence devices, penile implants, small or temporary joint replacements, urinary dilators, cannulas, elastomers, hydrogels, surgical instruments, dental instruments, tubings (such as intravenous tubes, breathing tubes, dental water lines, dental drain tubes, and feeding tubes), fabrics, paper, indicator strips (e.g., paper indicator strips or plastic indicator strips), adhesives (e.g., hydrogel adhesives, hot-melt adhesives, solvent-based adhesives, etc.), bandages, orthopedic implants, and/or any other device used in the medical field.

The term "medical devices" as used herein also includes any device which may be inserted or implanted into a human being or other animal, or placed at the insertion or implantation site such as the skin near the insertion or implantation site, and which includes at least one surface which is susceptible to colonization by biofilm-embedded microorganisms.

The term "medical devices" as used herein may also include any other surface in which it may be desirable or necessary to prevent biofilm-embedded microorganisms from growing or proliferating on at least one surface of the medical device, or to remove or clean biofilm-embedded microorganisms from the at least one surface of the medical device, such as the surfaces of equipment in operating rooms, emergency rooms, hospital rooms, clinics, bathrooms, etc.

In one specific embodiment, the biofilm-active and biofilm-penetrating composition of the present invention is integrated into an adhesive, such as tape, thereby providing an adhesive which may prevent growth or proliferation of biofilm-embedded microorganisms on at least one surface of the adhesive.

The term "implantable medical devices" as used herein may include orthopedic implants which may be inspected for contamination or infection by biofilm-embedded microorganisms using endoscopy.

The term "insertable medical devices" as used herein may include catheters and shunts which can be inspected without invasive techniques such as by endoscopy.

The medical devices may be formed of any suitable metallic or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubbers, plastics, polyesters, polyethylenes, polyurethanes, silicones, Gortex (polytetrafluoroethylene), Dacron® (polyethylene tetraphthalate), Teflon (polytetrafluoroethylene), latex, elastomers and Dacron® sealed with gelatin, collagen or albumin, and derivatives or combinations thereof.

The medical devices include at least one surface for applying the biofilm-active and biofilm-penetrating composition thereto.

Preferably, the biofilm-active and biofilm-penetrating composition is applied to the entire medical device.

The biofilm-active and biofilm-penetrating composition of the present invention preferably involves the use of taurolidine as the biofilm-active ingredient.

Taurolidine (bis(1,1-dioxoperhydro-1,2,4-thiadiazinyl-4)-methane) has antimicrobial and antilipopolysaccharide properties. It is derived from the amino acid taurine. Its immunomodulatory action is reported to be mediated by priming and activation of macrophages and polymorphonuclear leukocytes.

Taurolidine has been used to treat patients with peritonitis and as an antiendoxic agent in patients with systemic inflammatory response syndrome. It is a life-saving antimicrobial for severe abdominal sepsis and peritonitis. Taurolidine is active against a wide range of microorganisms that include gram-positive bacteria, gram-negative bacteria, fungi, mycobateria and also bacteria that are resistant to various antibiotics such as Methicillin-Resistant *Staphylococcus aureus* (MRSA), Vancomycin Intermediate *Staphylococcus aureus* (VISA), Vancomycin Resistant *Staphylococcus aureus* (VRSA), Oxacillin Resistant *Staphylococcus aureus* (ORSA), Vancomycin-Resistant Enterococci (VRE), etc. Additionally, taurolidine demonstrates some anti-tumor properties, with positive results seen in early-stage clinical investigations using the drug to treat gastrointestinal malignancies and tumors of the central nervous system.

Taurolidine is the active ingredient of antimicrobial catheter lock solutions for the prevention and treatment of Catheter-Related Blood Stream Infections (CRBSIs) and is suitable for use in all catheter-based vascular access devices. Bacterial resistance against taurolidine has never been observed in various studies.

Taurolidine acts by a non-selective chemical reaction. In aqueous solution, the parent molecule taurolidine forms an equilibrium with taurultam and N-hydroxymethyl taurultam, with taurinamide being a downstream derivative. The active moieties of taurolidine are N-methylol derivatives of taurultam and taurinamide, which react with the bacterial cell wall, cell membrane, and cell proteins, as well as with the primary amino groups of endo- and exotoxins. Microbes are killed and the resulting toxins are inactivated. The destruction time in vitro is 30 minutes. Pro-inflammatory cytokines and enhanced tumor necrosis factor (TNF) levels are reduced when used as a catheter lock solution. Taurolidine decreases the adherence of bacteria and fungi to host cells by destructing the fimbriae and flagella and thus prevent biofilm formation.

In the prior art, a dose of 5 g of taurolidine over 2 hours, given every 4 hours, for at least 48 hours, was delivered intravenously for the treatment of sepsis.

The biofilm-penetrating agent (e.g., long-chain or short-chain fatty acids or fatty alcohols) is included in the biofilm-active composition in amounts sufficient to penetrate, or break-up, the biofilm and provide the biofilm-active agent, antimicrobial agent, and/or antifungal agent (e.g., taurolidine) access to the biofilm-embedded microorganisms, thereby facilitating the removal of substantially all of the biofilm-embedded microorganisms from at least one surface of the medical device. While the biofilm-active agent may be 100% of the biofilm-active composition, preferably, the biofilm-active composition preferably also contains from at least about 0.01% to about 10% biofilm-penetrating agent by weight based upon the total weight of the biofilm-active composition being employed. In the preferred embodiment, the biofilm-active composition includes from at least about 0.5% to about 6% (by weight) biofilm-penetrating agent which is present to act as a penetrating enhancing agent. The biofilm-penetrating agent may be in the form of long-chain or short-chain fatty acids or fatty alcohols.

In one form of the invention, the biofilm-penetrating agent comprises at least one of a saturated fatty alcohol or fatty acid of 8-15 carbon atoms or an unsaturated fatty alcohol or fatty acid of 8-18 carbon atoms. Preferred penetration-enhancing fatty acids and fatty alcohols are those with 10-15 carbon atoms or any mixture thereof. Especially preferred penetration-enhancing fatty acids and fatty alcohols are those with 14 carbon atoms such as myristic acid and myristyl alcohol.

The term "base material" as used herein may include (i) a surface of the indwelling medical device to which the biofilm-active and biofilm-penetrating composition may be applied, and/or (ii) a carrier material carrying the biofilm-active and biofilm-penetrating composition to the indwelling medical device, e.g., a hydrogel.

In one preferred form of the invention, the base material may be any of a group of materials which effectively disperses the biofilm-penetrating agent at an effective concentration to penetrate, or break-up, the biofilm, thereby facilitating access of the biofilm-active agent, antimicrobial agents, and/or antifungal agents (e.g., the taurolidine) to the microorganisms embedded in the biofilm, and thus, removal of substantially all of the microorganisms from at least one surface of the medical device.

The term "base material" as used herein may also include any group of solutions which effectively disperse the biofilm-active agent and biofilm-penetrating agent at an effective concentration to form a biofilm-active and biofilm-penetrating composition coating for medical devices which substantially prevents the growth or proliferation of biofilm-embedded microorganisms on at least one surface of the medical device. In the case of the biofilm-active and biofilm-penetrating composition coating, preferably, the base material also facilitates the adhesion of the biofilm-active and biofilm-penetrating composition to at least one surface of the medical device and prevents the biofilm-active and biofilm-penetrating composition coating from being easily removed from the surface of the medical device, thereby facilitating the utilization of the biofilm-active and biofilm-penetrating composition to coat at least one surface of a medical device.

Examples of suitable base materials include, but are not limited to, buffer solutions, phosphate buffered saline, saline, water, polyvinyl, polyethylene, polyurethane, polypropylene, silicone (e.g., silicone elastomers and silicone adhesives), polycarboxylic acids, (e.g., polyacrylic acid, polymethacrylic acid, polymaleic acid, poly-(maleic acid monoester), polyaspartic acid, polyglutamic acid, alginic acid or pectinic acid), polycarboxylic acid anhydrides (e.g., polymaleic anhydride, polymethacrylic anhydride or polyacrylic acid anhydride), polyamines, polyamine ions (e.g., polyethylene imine, polyvinylarnine, polylysine, poly-(dialkylamineoethyl methacrylate), poly-(dialkylaminomethyl styrene) or poly-(vinylpyridine)), polyammonium ions (e.g., poly-(2-methacryloxyethyl trialkyl ammonium ion)), poly-(vinylbenzyl trialkyl ammonium ions), poly-(N.N.-alkylypyridinium ion) or poly-(dialkyloctamethylene ammonium ion) and polysulfonates (e.g. poly-(vinyl sulfonate) or poly-(styrene sulfonate)), collodion, nylon, rubbers, plastics, polyesters, Gortex (polytetrafluoroethylene), Dacron® (polyethylene tetraphthalate), Teflon polytetrafluoroethylene), latex, and derivatives thereof, elastomers and Dacron® sealed with gelatin, collagen or albumin, cyanoacrylates, methacrylates, papers with porous barrier films, adhesives (e.g., hot-melt adhesives, solvent-based adhesives, and adhesive hydrogels), fabrics, and crosslinked and non-crosslinked hydrogels, and any other polymeric materials which facilitate dispersion of the biofilm-active and biofilm-penetrating agents and adhesion of the biofilm-active and biofilm-penetrating composition coating to at least one surface of the medical device. Linear copolymers, cross-linked copolymers, graft polymers, and block polymers, containing monomers as constituents of the above exemplified polymers, may also be used.

The term "polyvinyl" as used herein may include any of a group of polymerized vinyl compounds such as PV-coA-coVA (Polyvinyl butyryl-co-vinyl alcohol-co-vinylacetate), PV-coA-coVA plus hydroxylapatite, PVP (Polyvinyl pyrrolidone), PVP-coVA (Polyvinyl pyrrolidone co-vinyl acetate dissolved in 2-propanol) and combinations thereof.

The term "nylon" as used herein may include any of a group of synthetic long-chain polymeric amides with recurring amide groups having great strength and elasticity, such as polycaprolactam, polylauryl-lactam and polyhexamethylene sebacamide.

In one preferred form of the invention, the base material comprises a hydrogel. In one particularly preferred form of the invention, the hydrogel comprises hyaluronic acid.

Thus it will be seen that, in one form of the invention, there is provided a biofilm-active composition for inhibiting the growth of biofilms on medical devices, wherein the biofilm-active composition comprises at least one biofilm-active agent (e.g., taurolidine or a derivative thereof) and at least one biofilm-penetrating agent (e.g., long-chain or short-chain fatty acids or fatty alcohols such as myristic acid and myristyl alcohol). In one form of the invention, the biofilm-active and biofilm-penetrating agents are combined with a base material (e.g., a hydrogel such as hyaluronic acid) which adheres to the medical device and which releases the biofilm-active and biofilm-penetrating agents. In another form of the invention, the biofilm-active and biofilm-penetrating composition is applied to a surface of the medical device for inhibiting the growth of biofilms on the medical device.

Examples

The following examples are offered by way of illustration and are not intended to limit the invention in any manner. For example, other biofilm-active and biofilm-penetrating compositions may be formed having lower concentrations of biofilm-active and biofilm-penetrating agents which are capable of preventing or removing microorganism growth along at least one surface of a medical device. Further, other biofilm-active and biofilm-penetrating compositions may be formed at concentrations sufficient for preventing or removing microorganism growth along at least one surface of a medical device depending on the cause of the microorganism contamination.

Hyaluronic Acid Hydrogel Preparation

Formulations of taurolidine in aqueous solutions of hyaluronic acid (HA) crosslinked with 1,4-butanediol diglycidyl ether (BDDE) were prepared. 3% taurolidine solutions were formulated in aqueous solutions of crosslinked HA of three molecular weights: low molecular weight (LMW) 21-40 kDa, medium molecular weight (MMW) 310-450 kDa and high molecular weight (HMW) 750 kDa-1.0 MDa. Control formulations were prepared without addition of the taurolidine. 1.5% myristic acid was added to enhance the interaction with the explant. The compositions of each formulation are given in Table 1 below.

Biofilm Porcine Explant Model

The ex vivo model of biofilm on porcine skin explants used in this study consisted of 12 mm biopsied explants (3-4 mm thick) prepared from freshly harvested, shaved and cleaned porcine skin obtained from a local abattoir (Chiefland Custom Meat, Trenton, FL). The mechanically created "wound bed" (3 mm high speed, round, cutter bit; Dremel®, Robert Bosch Tool Corporation, Racine, WI) was 3 mm in diameter and approximately 1.5 mm in depth at the centre of each explant. The chlorine gas (45 minutes)-sterilised explants were placed on soft trypticase soy agar (TSA) plates containing 0.5% agar and 50 µg/ml gentamicin. The addition of 50 µg/ml gentamicin (approximately 30× minimal inhibitory concentration) functions to limit bacterial growth to the explant and inhibits penetration of *Pseudomonas aeruginosa* (PAO1) biofilm through the bottom of the explant for up to 5-6 days, depending on the thickness of the explant. The partial-thickness "wound bed" of the explants was inoculated with 10 µl early-logarithmic (log)-phase PAO1 suspension culture (106 CFU) and cultured at 37° C. with 5% CO2 and saturated humidity. Explants were transferred daily to fresh soft TSA plates containing 0.5% agar and antibiotic (to maintain moisture) until the desired biofilm maturity was achieved. They were submerged in tryptic soy broth (TSB) media containing 200 µg/ml gentamicin for 24 hours to kill planktonic PAO1 in studies used to assess antimicrobial efficacy of test agents specifically against the highly antibiotic tolerant biofilm subpopulation attached to the porcine explants, described in more complete detail below. For clarity, exposure times to the test agents were expressed in hours and the length of biofilm culture incubation prior to treatment was expressed in days.

The bacterial load of the explants was determined in each of the assays of this study as follows: each explant was aseptically placed into a 15 ml sterile tube (on ice) containing cold 7 ml sterile phosphate-buffered saline (PBS) with 5 µl/l Tween-80. The explants in the tubes were sonicated with a 23 kHz ultrasonic dismembrator (Model 100, Fisher Scientific, Pittsburgh, PA) probe for 30 seconds at approximately 20 W on ice, which liberated bacteria from the biofilm into the suspension. The setting on the dismembrator probe tip was adjusted to maintain the target watt output. The sonication probe was disinfected between samples using cold 70% ethanol (ETOH) and rinsed with cold sterile PBS (on ice). Serial dilutions of the bacterial suspension were plated in triplicate on TSA plates and incubated overnight at 37° C. with 5% CO2 and saturated humidity. Colonies were counted from the plates to determine the colony forming unit per milliliter (CFU/ml) of the sonicated explant bacterial suspension.

Assessment of the Efficacy of Antimicrobial Hydrogel Compositions Against PAO1 Biofilm 72-Hour Continuous Exposure Antimicrobial efficacy assays against mature PAO1 biofilm attached to the skin were performed with 72 hour continuous exposure. PAO1 biofilms cultured 3 days on porcine skin explants were transferred to sterile 24 well microtiter plates and each explant was treated for 24 hours by submersion in 2 ml TSB media containing 200 µg/ml gentamicin. This level of antibiotic was used because it was capable of restraining the PAO1 biofilm to the surface of the explant. The media in the wells remained clear and no viable bacteria were detected in the media or the microtiter wells during or after treatment of the explants. As stated previously, pre-treatment with high antibiotics allows subsequent assessment of the antimicrobial efficacy of the dressing agents directly against the antibiotic tolerant biofilm subpopulation. The antibiotic pre-treated explants, containing only mature PAO1 biofilm, were each rinsed thrice with 2 ml of sterile PBS, washed in 2 ml PBS for 10 minutes and then rinsed thrice with 2 ml PBS to remove unattached bacteria. The rinsed biofilm explants were transferred to soft TSA plates containing 0.5% agar and 50 µg/ml gentamicin (three or four explants per plate).

The biofilm explants that were used to determine the "standard" baseline total microbial load were covered with sterile ddH2O-saturated (5 ml) "wet" cotton gauze sponge (2"×2"). The rest of the biofilm explants were covered and treated with 1 ml of Hyaluronic Acid loaded hydrogels shown in Table 1. The treated biofilm explants were each processed by sonication in 7 ml PBS with 5 µl/l Tween 80, as previously described. Bacterial suspensions were immediately serially diluted and plated in triplicate on TSB, and the average CFU/ml was determined for the 7 ml bacterial suspension from each explant. A minimum of three separate trials were performed for each antimicrobial hydrogel composition reported in this study.

Time-Course Assay

The time-course studies were performed to determine the antimicrobial efficacy of the taurolidine hydrogels on biofilm maturity. The biofilm explants were continuously exposed to the antimicrobial hydrogel composition for 72 hours. The treated explants were each processed by sonication in 7 ml PBS with 5 µl/l Tween 80 as previously described. Bacterial suspensions were immediately serially diluted and plated in triplicate on TSB, and the average CFU/ml was determined for the 7 ml bacterial suspension from each explant.

6 samples from the Cambridge Polymer Group were used.
Day 1: PA01 OD600=0.243 Conc=1.21E08
Day 3: put 3 day cultured explants in 24 well treat with 1 ml different solution.
Day 4: cell count

TABLE 1

| PA01 | AVG | STDEV |
|---|---|---|
| Total (3 day cultured PA01 explants) | 1.47E+09 | 1.43E+08 |
| Biofilm, 200 ug/ml Gentamicin | 3.45E+07 | 4.68E+07 |
| 13146-1, LMW HA cntr, no drug, 1.5% Myristic acid (ST Jul. 27, 2016) | 9.32E+06 | 4.12E+06 |

TABLE 1-continued

| PA01 | AVG | STDEV |
|---|---|---|
| 13146-2, MMW HA cntr, no drug, 1.5% Myristic acid (ST Jul. 27, 2016) | 4.18E+07 | 3.65E+07 |
| 13146-3, HMW HA cntr, no drug, 1.5% Myristic acid (ST Jul. 27, 2016) | 5.78E+07 | 6.60E+07 |
| 13146-4, LMW HA cntr, 3% drug, 1.5% Myristic acid (ST Jul. 27, 2016) | 7.22E+01 | 1.03E+02 |
| 13146-5, MMW HA cntr, 3% drug, 1.5% Myristic acid (ST Jul. 27, 2016) | 4.44E+01 | 7.70E+01 |
| 13146-6,, HMW HA cntr, 3% drug, 1.5% Myristic acid (ST Jul. 27, 2016) | 0.00E+00 | 0.00E+00 |

These results show that taurolidine-loaded hydrogels effectively penetrate and break up the biofilm and kills biofilm-embedded microorganisms such as *Pseudomonas aeruginosa* (PA01). See FIG. 1.

Additional Testing of the Efficacy of a Taurolidine Formulation Comprising the Biofilm-Penetrating Agent Myristic Acid and Taurolidine in a Hyaluronic Acid Base Material Mature biofilms from *Pseudomonas aeruginosa* were prepared on pig-skin explants in order to test the efficacy of hyaluronic acid hydrogels containing taurolidine and myristic acid. See Table 2 below, which provides the compositions of each formulation.

TABLE 2

| Sample | Hyaluronic Acid (MW) | Taurolidine Concentration (%) | Myristic Acid Concentration (%) |
|---|---|---|---|
| 13079-1 | Low | 0 | 1.5 |
| 13079-2 | Medium | 0 | 1.5 |
| 13079-3 | High | 0 | 1.5 |
| 13079-4 | Low | 1.5 | 1.5 |
| 13079-5 | Medium | 1.5 | 1.5 |
| 13079-6 | High | 1.5 | 1.5 |
| 13079-7 | Low | 3.0 | 1.5 |
| 13079-8 | Medium | 3.0 | 1.5 |
| 13079-9 | High | 3.0 | 1.5 |

Figure 2:
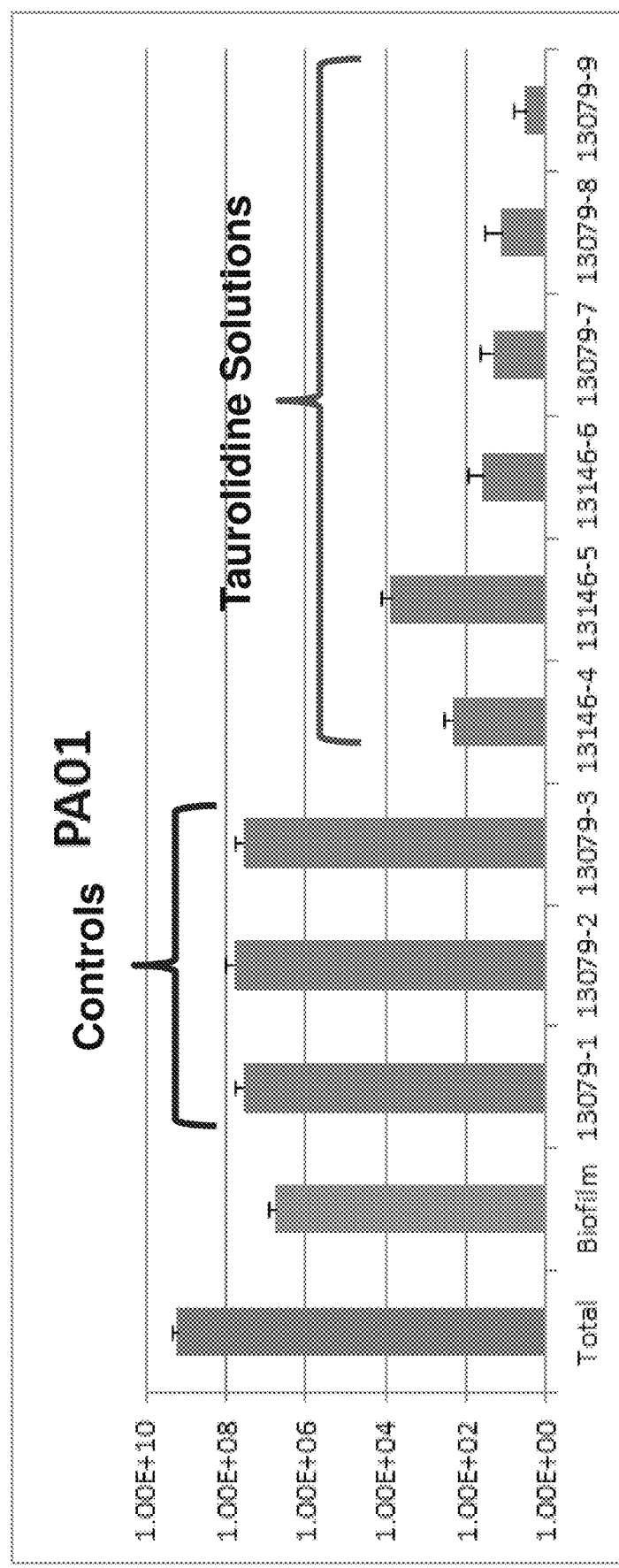
FIG. 2 is another graph showing the activity of taurolidine-loaded hydrogels against biofilm on a Pig Skin Explant Model.

FIG. 2 is a graph showing the efficacy of biofilm-active compositions, comprising taurolidine and myristic acid carried by hyaluronic acid hydrogels, against biofilms on the pig skin explant models. These results show that biofilm-active compositions comprising taurolidine and myristic acid carried by hyaluronic acid hydrogels can effectively penetrate and break-up biofilms and kill biofilm embedded microorganisms such as *Pseudomonas aeruginosa* (PA01).

FIG. 3 is a table listing 15 different formulations, as follows:

| CORMEDIX-18 |
|---|
| Formulation 1 - Low Molecular Weight (LMW) Hyaluronic Acid (HA) Control (Cntr); |
| Formulation 2 - Medium Molecular Weight (MMW) Hyaluronic Acid (HA) Control (Cntr); |
| Formulation 3 - High Molecular Weight (HMW) Hyaluronic Acid (HA) Control (Cntr); |
| Formulation 4 - Low Molecular Weight (LMW) Hyaluronic Acid (HA) and 0.5% Taurolidine; |
| Formulation 5 - Medium Molecular Weight (MMW) Hyaluronic Acid (HA) and 0.5% Taurolidine; |
| Formulation 6 - High Molecular Weight (HMW) Hyaluronic Acid (HA) and 0.5% Taurolidine; |
| Formulation 7 - Low Molecular Weight (LMW) Hyaluronic Acid (HA) and 1.0% Taurolidine; |
| Formulation 8 - Medium Molecular Weight (MMW) Hyaluronic Acid (HA) and 1.0% Taurolidine; |
| Formulation 9 - High Molecular Weight (HMW) Hyaluronic Acid (HA) and 1.0% Taurolidine; |

| CORMEDIX-18 |
|---|
| Formulation 10 - Low Molecular Weight (LMW) Hyaluronic Acid (HA) and 1.5% Taurolidine; |
| Formulation 11 - Medium Molecular Weight (MMW) Hyaluronic Acid (HA) and 1.5% Taurolidine; |
| Formulation 12 - High Molecular Weight (HMW) Hyaluronic Acid (HA) and 1.5% Taurolidine; |
| Formulation 13 - Low Molecular Weight (LMW) Hyaluronic Acid (HA), 1.0% Taurolidine and 0.25% Myristic Acid (MRA); |
| Formulation 14 - Medium Molecular Weight (MMW) Hyaluronic Acid (HA), 1.0% Taurolidine and 0.25% Myristic Acid (MRA); and |
| Formulation 15 - High Molecular Weight (HMW) Hyaluronic Acid (HA), 1.0% Taurolidine and 0.25% Myristic Acid (MRA). |

Figure 4:
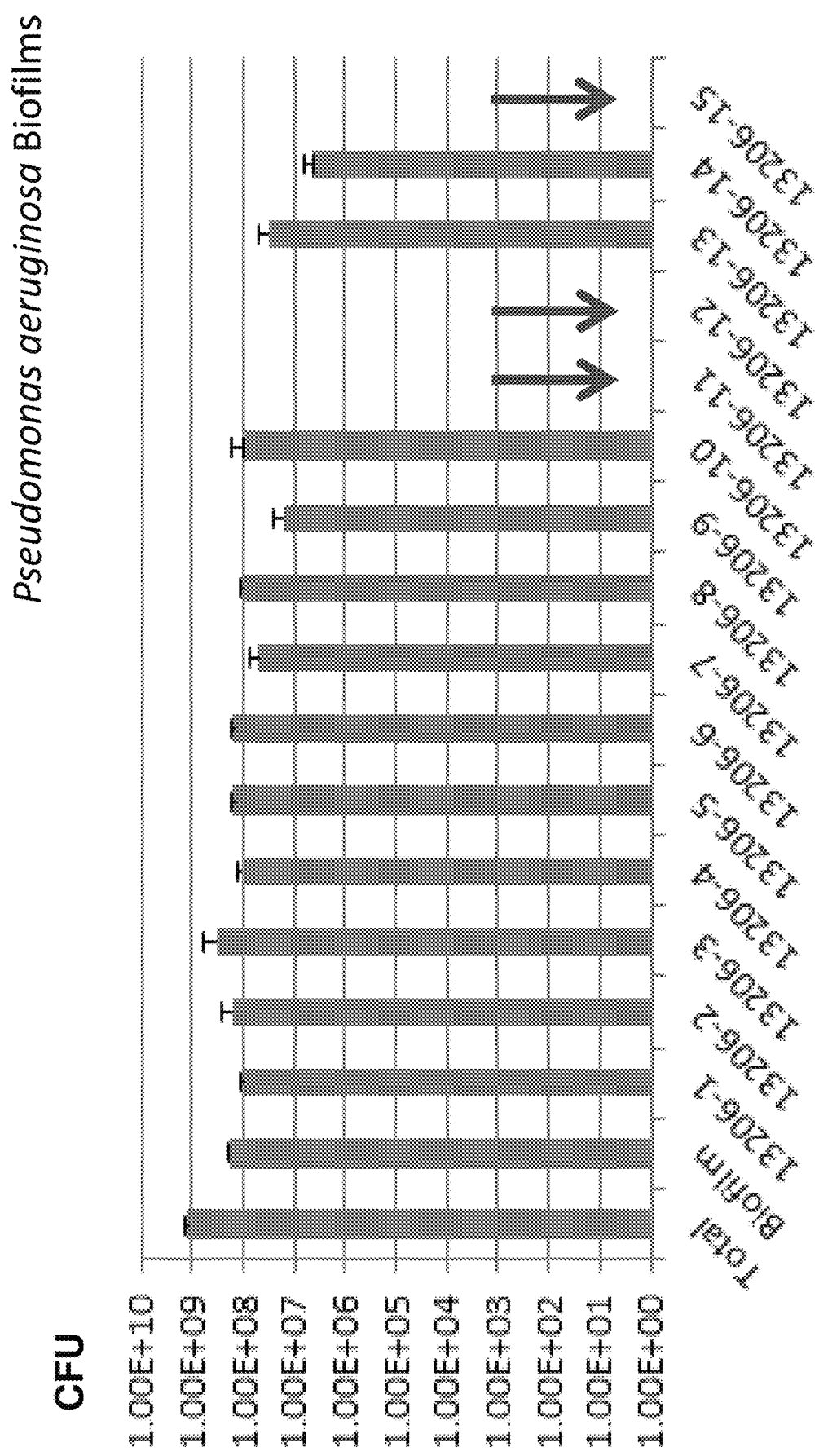
FIG. 4 is another graph showing the activity of taurolidine-loaded hydrogels against biofilm on a Pig Skin Explant Model.

Formulations 11, 12 and 15 have proven to be highly efficacious against biofilms on a pig skin explant model (i.e., Formulations 11, 12 and 15 all provided an effectiveness of less than 1.00E+00). See FIG. 4.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for killing *Pseudomonas aeruginosa* on at least one surface of a catheter, the method comprising the steps of: (a) providing a bio-film active composition comprising: taurolidine, wherein the concentration of the taurolidine, is 0.5% by weight, 1.0% by weight, 1.5% by weight, or 3.0% by weight of the total weight of the bio-film active composition;

a biofilm-penetrating agent comprising myristic acid, wherein the concentration of the myristic acid is about 1.5% by weight of the total weight of the bio-film active composition; and a base material, wherein the base material comprises a hydrogel comprising hyaluronic acid having a molecular weight of 750 kDa to 1.0 MDa; and (b) delivering the bio-film active composition to the at least one surface of a catheter in a sufficient amount and for a sufficient period of time to kill *Pseudomonas aeruginosa* on at least one surface of the catheter.

2. A method according to claim 1 wherein the biofilm-active composition is formed by mixing taurolidine, the myristic acid and the base material.

3. A method according to claim 1 wherein the biofilm-active composition is delivered to the at least one surface of the catheter by contacting the at least one surface of the catheter for a period of time sufficient to kill *Pseudomonas aeruginosa* on the at least one surface of the catheter.

4. A method according to claim 1 wherein the biofilm-active composition is delivered to the at least one surface of the catheter by integrating the biofilm-active composition within the catheter.

5. A method according to claim 1 wherein the hyaluronic acid is crosslinked hyaluronic acid.

* * * * *